(12) United States Patent
Rüdenauer et al.

(10) Patent No.: US 9,765,001 B2
(45) Date of Patent: Sep. 19, 2017

(54) METHOD FOR PRODUCING ARYLPROPENES

(71) Applicant: BASF SE (Herzog Fiesser & Partner), Ludwigshafen (DE)

(72) Inventors: Stefan Rüdenauer, Weinheim (DE); Andreas Lanver, Mannheim (DE); Ralf Pelzer, Fürstenberg (DE); Klaus Ebel, Heddesheim (DE); Thomas Fenlon, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/111,841

(22) PCT Filed: Jan. 16, 2015

(86) PCT No.: PCT/EP2015/050792
§ 371 (c)(1),
(2) Date: Jul. 15, 2016

(87) PCT Pub. No.: WO2015/107156
PCT Pub. Date: Jul. 23, 2015

(65) Prior Publication Data
US 2016/0332944 A1    Nov. 17, 2016

(30) Foreign Application Priority Data
Jan. 17, 2014 (EP) .................................. 14151641

(51) Int. Cl.
C07C 41/18    (2006.01)
(52) U.S. Cl.
CPC .................................. *C07C 41/18* (2013.01)
(58) Field of Classification Search
CPC .................................................... C07C 41/18
See application file for complete search history.

(56) References Cited

U.S. PATENT DOCUMENTS

| 4,026,951 | A | 5/1977 | Bauer et al. |
|---|---|---|---|
| 8,853,471 | B2 | 10/2014 | Rudenauer et al. |
| 8,940,940 | B2 | 1/2015 | Dehn et al. |
| 8,993,812 | B2 | 3/2015 | Rudenauer |
| 9,029,605 | B2 | 5/2015 | Schaub et al. |
| 9,062,136 | B2 | 6/2015 | Porta Garcia et al. |
| 9,085,526 | B2 | 7/2015 | Schaub et al. |
| 9,139,549 | B2 | 9/2015 | Stork et al. |
| 9,217,121 | B2 | 12/2015 | Rudenauer et al. |
| 9,340,754 | B2 | 5/2016 | Rudenauer et al. |
| 9,452,962 | B2 | 9/2016 | Pelzer et al. |
| 2008/0045752 | A1 | 2/2008 | Sinha et al. |
| 2016/0060238 | A1 | 3/2016 | Stork et al. |
| 2016/0068500 | A1 | 3/2016 | Stork et al. |
| 2016/0186008 | A1 | 6/2016 | Klopsch et al. |
| 2016/0213582 | A1 | 7/2016 | Rudenauer et al. |

FOREIGN PATENT DOCUMENTS

| CN | 102491884 A | 6/2012 |
|---|---|---|
| CN | 103058835 A | 4/2013 |
| DE | 2418974 B1 | 9/1975 |
| RU | 2064920 C1 | 8/1996 |
| SU | 261380 | 1/1970 |
| SU | 355144 | 1/1972 |
| WO | WO-2015018793 A1 | 2/2015 |

OTHER PUBLICATIONS

U.S. Appl. No. 61/759,487, filed Feb. 1, 2013.
Bauer et al., "2.6 Phenols and Phenol Derivatives", Common Fragrance and Flavor Materials, 2001, 4th Edition, Wiley-VHC, pp. 125-141.
Maslozhirovaya Promyshlennost, 1974, vol. 9, pp. 29-30.
International Preliminary Report on Patentability for PCT/EP2015/050792 mailed Oct. 19, 2015.
International Search Report for PCT/EP2015/050792 mailed Oct. 22, 2015.

*Primary Examiner* — Rosalynd Keys
(74) *Attorney, Agent, or Firm* — Drinker Biddle & Reath LLP

(57) ABSTRACT

The present invention relates to a process for preparing arylpropenes, especially 1-methoxy-4-(1-propenyl)benzene (anethole), by means of thermolysis of the corresponding 1,1-diarylpropanes.

14 Claims, No Drawings

METHOD FOR PRODUCING ARYLPROPENES

CROSS-REFERENCE TO RELATED APPLICATIONS

This application is a national stage application (under 35 U.S.C. §371) of PCT/EP2015/050792, filed Jan. 16, 2015, which claims benefit of European Application No. 14151641.9, filed Jan. 17, 2014, both of which are incorporated herein by reference in their entirety.

The present invention relates to a process for preparing arylpropenes, especially 1-methoxy-4-(1-propenyl)benzene (anethole), by means of thermolysis of the corresponding 1,1-diarylpropanes.

BACKGROUND OF THE INVENTION

Anethole (1-methoxy-4-(1-propenyl)benzene) is of great commercial interest as a fragrance and flavouring because of its characteristic aniseed odor. More particularly, anethole is used as fragrance in washing and cleaning compositions or cosmetics, and as flavoring in the foods industry.

The preparation of anethole has long been known in the prior art. For instance, one way of obtaining anethole is from natural sources, for example from fennel oil or anise oil—see RU2064920 and CN102491884.

However, the production of fragrances from natural sources is usually costly, and the amounts thus obtainable are limited. Moreover, the purity or production volume of these fragrances often varies because of variable environmental conditions in the production of the raw materials from which they are isolated. There is therefore a great interest in at least partly replacing fragrances from natural sources with substances obtainable by synthetic means.

The prior art discloses various synthetic processes for preparation of anethole. For example, Bauer et al., Common Fragrance and Flavor Materials, 2001, 4th Edition, Wiley-VHC, describes the preparation of anethole by a base-catalyzed rearrangement of 1-methoxy-4-allylbenzene (estragiol).

A further method of preparing anethole, as described, for example, in SU261380 and SU355144, includes a Friedel-Crafts acylation of anisole with propionyl halides or propionic anhydride, followed by the reduction of the carbonyl group and subsequent elimination of water. The acylation of anisole with propionic anhydride can be effected, inter alia, with $ZnCl_2$ and $FeCl_3$ (see Maslozhirovaya Promyshlennost (1974), volume 9, pages 29-30).

CN103058835 describes a process for synthesizing anethole, in which a Friedel-Crafts reaction proceeding from anisole and propionyl chloride is conducted, followed by a reduction of the carbonyl group to the corresponding alcohol with the aid of $NaBH_4$ and subsequent elimination of water with p-TsOH and $KHSO_4$.

DE 2418974 B1 describes a process for preparing anethole, in which, in a first step, anisole is condensed with propionaldehyde in the presence of acidic catalysts to give a mixture of bis(methoxyphenyl)propanes. In a second step, the condensation products are cleaved into p-anethole, or o-anethole and anisole, by using catalytic amounts of acid and by heating to temperatures of 100 to 300° C. in the liquid phase. Specifically, the cleavage of the bis(methoxyphenyl) propanes is conducted in the presence of a catalytic amount of concentrated phosphoric acid at 200° C., with distillative removal of the cleavage products formed at about 5 to 30 Torr. Pure p-anethole is obtained from the distillate by fractional distillation. A disadvantage is that the bis (methoxyphenyl)-propanes are not completely cleaved, i.e. are only partially converted. Moreover, only moderate yields of anetholes are achieved. The long residence time of the bis-(methoxyphenyl)propanes and the cleavage products at elevated temperature additionally leads to increased formation of by-products, unwanted isomers, and oligomers and polymers.

SUMMARY OF THE INVENTION

It is an object of the present invention to provide an improved process for preparing arylpropenes, especially anethole, with which the aforementioned disadvantages can be avoided. Moreover, the process should be simple and efficient, in order to enable inexpensive preparation of arylpropenes.

This object is surprisingly achieved by a process for preparing arylpropenes of the general formula (I)

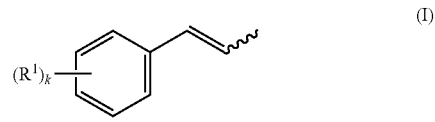

in which
k has the values of 0, 1, 2 or 3 and
$R^1$ is independently selected from $C_1$-$C_6$-alkoxy, di($C_1$-$C_6$-alkyl)amines and hydroxyl, comprising the thermolysis of at least one 1,1-diarylpropane compound of the general formula (II)

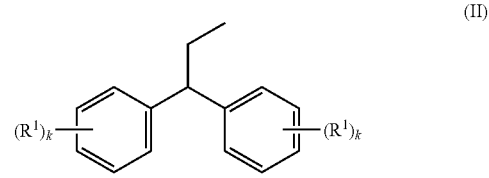

in which k and $R^1$ have the definitions given above,
wherein the compound of the formula II in the gas phase is contacted with at least one solid acidic oxidic catalyst in a reaction zone.

Because the reaction is conducted in the gas phase at high temperatures, the residence time of the feedstocks and the cleavage products in the reaction zone can be kept very short. The formation of by-products can thus be greatly reduced. The process according to the invention can keep the formation of unwanted isomers low, which leads to good product selectivities. In spite of the short residence time of the feedstocks in the reaction zone, it is possible by the process of the invention to achieve high conversions. The process of the invention can be conducted continuously and is notable for its simplicity and economic viability.

The arylpropenes of the general formula I can be prepared by the process of the invention from readily available starting materials, which means that they can be provided on the industrial scale without any problem.

DETAILED DESCRIPTION OF THE INVENTION

In the context of the present invention, the expression "$C_1$-$C_6$-alkoxy" encompasses straight-chain or branched $C_1$-$C_6$-alkoxy groups comprising 1 to 6 carbon atoms, preferably 1 to 4 carbon atoms, which are bonded via an oxygen atom. These include methoxy, ethoxy, n-propoxy, 1-methylethoxy, n-butoxy, 1-methylpropoxy, 2-methylpropoxy, 1,1-dimethylethoxy, n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and the like. More particularly $C_1$-$C_6$-alkoxy encompasses straight-chain or branched alkyloxy groups having 1, 2 or 3 carbon atoms ($C_1$-$C_3$-alkoxy).

In the context of the present invention, the expression "di-($C_1$-$C_6$-alkyl)-amine" relates to alkylamines substituted by two $C_1$-$C_6$-alkyl radicals. The $C_1$-$C_6$-alkyl radicals each independently comprise straight-chain or branched $C_1$-$C_6$-alkyl groups. These include methyl, ethyl, propyl, isopropyl, n-butyl, isobutyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl and the like. More particularly, the $C_1$-$C_6$-alkyl radicals independently encompass straight-chain or branched alkyl groups having 1, 2 or 3 carbon atoms ($C_1$-$C_3$-alkyl).

In preferred embodiments, in the compounds of the general formula I and II used in the process of the invention, k is 1 and the $R^1$ radical is hydroxyl or $C_1$-$C_6$-alkoxy, especially hydroxyl or $C_1$-$C_4$-alkoxy and specifically hydroxyl or methoxy.

More particularly, the compounds of the general formula II used in the process of the invention comprise, to an extent of at least 50 mol %, especially to an extent of at least 80 mol %, based on the total amount of the compounds of the formula II, compounds of the general formula (II.a)

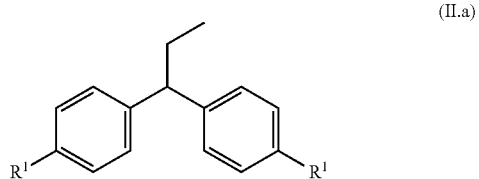

(II.a)

in which both $R^1$ are the same and have the definitions given above and are especially hydroxyl or $C_1$-$C_4$-alkoxy and specifically hydroxyl or methoxy. As well as the compound of the general formula II.a, the compounds of the formula II may especially also comprise regioisomers of II.a, i.e. compounds of the formula I with k=1, in which the $R^1$ radicals are in the 2 or 3 position, based on the bonding site of the phenyl rings.

In a particularly preferred embodiment, the compounds of the general formula II used in the process of the invention comprise, to an extent of at least 50 mol %, especially to an extent of at least 80 mol %, based on the total amount of the compounds of the formula II, 1,1-bis(4-methoxyphenyl)propane and 1,1-bis(4-hydroxyphenyl)propane.

In the process of the invention, the 1,1-diarylpropane compound of the general formula II is contacted in the gas phase with at least one solid acidic oxidic catalyst in the reaction zone, which results in cleavage thereof to give the arylpropenes of the general formula I.

The arylpropenes of the general formula I prepared by the process of the invention generally take the form of cis/trans isomer mixtures or else of regioisomer mixtures, for example mixtures of ortho- and para-substituted compounds. For example, in the thermal cleavage of the 1,1-bis(4-methoxyphenyl)propane feedstock, not only is the desired p-trans-anethole formed, but also the cis isomer (p-cis-anethole) and a cis/trans isomer mixture of the corresponding ortho-substituted anethole (o-cis-anethole, or o-trans-anethole). A further cleavage product likewise formed is anisole.

In the context of the present invention, this cleavage is also referred to as thermolysis or thermal cleavage.

The thermal cleavage can generally be effected at ambient pressure or reduced or elevated pressure. Preferably, the thermal cleavage is conducted at ambient pressure or reduced pressure, for example at a pressure in the range from 0.1 to 2.0 bar, especially within a range from 0.8 to 1.1 bar.

In the context of the present invention, the expression "in the gas phase" means that the thermolysis is conducted at a temperature at which the majority, e.g. at least 99%, of the 1,1-diarylpropane compounds of the general formula II used, is in the gas phase. Ideally, the temperature in the reaction zone is at least 5° C., especially 10° C., specifically 15° C., e.g. 15 to 30° C., above the corresponding boiling temperature of the 1,1-diarylpropane compounds of the general formula II used at the pressure that exists in the reaction zone.

In the process of the invention, the temperature in the reaction zone is typically in the range from 250° C. to 650° C. Preferably, the temperature in the reaction zone is in the range from 300° C. to 600° C., more preferably in the range from 320° C. to 550° C.

The thermal cleavage can be effected in the absence or presence of a solvent S. In a preferred embodiment, the reaction zone is supplied, together with the compound of the formula II, additionally with at least one solvent S.

If the thermal cleavage is conducted in the presence of at least one solvent S, this is generally an inert solvent(s) having a boiling point under the reaction temperature chosen, for example, within the range from 30° C. to 200° C., especially within the range from 60 to 150° C. In the context of the present invention, an inert solvent is understood to mean a solvent which does not enter into any reaction with the compounds involved in the cleavage under the reaction conditions chosen.

Suitable inert solvents are, for example, aliphatic hydrocarbons, halogenated aliphatic hydrocarbons, aromatic and substituted aromatic hydrocarbons, ethers, alkyl nitriles, and also alcohols or water, and mixtures thereof. Preferably, the solvent S is selected from aliphatic hydrocarbons such as pentane, hexane, heptane, ligroin, petroleum ether or cyclohexane, halogenated hydrocarbons such as dichloromethane, trichloromethane, tetrachloromethane, aromatic hydrocarbons such as benzene, toluene, xylene, halogenated aromatic hydrocarbons such as chlorobenzene, dichlorobenzenes, ethers such as diethyl ether, methyl tert-butyl ether, dibutyl ether, tetrahydrofuran or dioxane, $C_1$-$C_4$-alkyl nitriles such as acetonitrile or propionitrile, alcohols such as methanol, ethanol, water and mixtures thereof. More preferably, the solvent S is selected from diethyl ether, methyl tert-butyl ether, tetrahydrofuran, acetonitrile and water. More preferably, the solvent S comprises water to an extent of at least 0.3% by weight, based on the total amount of solvent S used. In particular, the solvent S is water.

If the thermal cleavage is conducted in the presence of at least one solvent S, the mass ratio of solvent S to the compound of the formula II is in the range from 20:1 to 1:100. Preferably, the mass ratio of solvent S to the compound of the formula II is in the range from 10:1 to 1:50. More preferably, the mass ratio of solvent S to the compound of the formula II is in the range from 2:1 to 1:50.

The solid oxidic catalyst used in the process of the invention comprises acidic solid oxidic materials.

Suitable solid oxidic materials are, for example, metal oxides and semimetal oxides of aluminum, of magnesium, of zinc, of titanium, of zirconium, of hafnium, of silicon, of cerium or of lanthanum, mixed oxides of these metals and oxide mixtures. Examples of such oxides are aluminum oxide, magnesium oxide, titanium dioxide, zinc(IV) oxide, cerium oxide, lanthanum oxide and silicon dioxide, and mixtures thereof. Preferably, the solid oxidic catalyst used in the process of the invention is silicon dioxide, especially silica.

Preferred oxidic catalysts have a specific BET surface area, determined by means of nitrogen adsorption at 77 K according to DIN ISO 9277 2003-5, in the range from 100 to 500 m$^2$/g.

Preferably, the catalyst is an acidic metal oxide or semimetal oxide or a metal or semimetal oxide which has been impregnated with an inorganic acid, for example with nitric acid, sulfuric acid or phosphoric acid.

In a particularly preferred embodiment of the process of the invention, the solid oxidic catalyst is a silica which has optionally been impregnated with one or more inorganic acids, for example with nitric acid, sulfuric acid or phosphoric acid.

The catalyst may be a powder, a regularly or irregularly shaped granular material, for example catalyst strands, or a shaped body. The catalyst is preferably used in the form of strands. Usually, the catalyst strands have a diameter in the range from 0.5 to 10 mm, especially in the range from 0.5 to 3 mm.

Preferably, the process of the invention is conducted in continuous mode, in which case the compound of the formula II is conducted continuously through the reaction zone comprising the solid oxidic catalyst.

In this case, the compound of the formula II is generally conducted through the reaction zone with a catalyst load of 0.01 to 5 kg of compound II per kg of catalyst and hour, preferably of 0.02 to 2 kg of compound II per kg of catalyst and hour, and especially at 0.05 to 1 kg of compound II per kg of catalyst and hour.

Preferably, the compound II is supplied to the reaction zone with the aid of a carrier gas. The carrier gas used is preferably an inert gas. In the context of the present invention, an inert gas is understood to mean a gas which does not enter into any reaction with the compounds involved in the cleavage under the reaction conditions chosen.

Preferably, in the process of the invention, the carrier gas used is He, Ar or $N_2$, especially $N_2$.

The volume flow rate of the carrier gas relative to the feedstocks (reactants and S) is typically in the range from 10:1 to 10000:1, preferably in the range from 100:1 to 5000:1 and especially in the range from 800:1 to 4000:1.

In a preferred embodiment of the process of the invention, the compounds of the formula II are supplied continuously to the reaction zone and the reaction product is quenched immediately after leaving the reaction zone. The quenching is generally effected by a downstream cooler. The cooler is typically directly connected to the reaction zone.

The reaction zone may be configured in the forms that are standard for gas phase reactions. In general, the reaction zone is a cylindrical reactor arrangement, for example a reaction tube filled with the catalyst. The filling may be a fixed bed, fluidized bed or packing. The reaction zone may be vertical or horizontal. In the case of a vertical arrangement, the compound of the formula II may be conducted through the reaction zone in an ascending or descending manner. Preferably, the reaction zone is configured as a tube, where the ratio of length to internal diameter is at least 3:1. Preferably, the ratio of length to internal diameter is in the range from 3:1 to 100:1, especially in the range from 5:1 to 10:1.

The reactor arrangement comprising the reaction zone typically has means of heating the reaction zone, for example an electrical heater or induction heating.

Preferably connected upstream of the reaction zone is an evaporator arrangement in which the compound of the formula II and optionally the solvent are evaporated and thus converted to the gas phase.

Preferably, at least one means of quenching the reaction product is connected immediately downstream of the reaction zone, for example a jacketed coil condenser or a cold trap.

The reaction products prepared by the process of the invention, which are generally in condensed form, can be purified by standard methods that are known to be relevant by the person skilled in the art, for example extraction, distillation, crystallization or chromatographic separation methods.

As already mentioned, the arylpropenes of the general formula I prepared by the process of the invention are generally present in the form of cis/trans isomer mixtures or else of regioisomer mixtures, for example mixtures of the ortho- and para-substituted compounds.

The separation of the individual isomers is generally possible by fractional distillation or by chromatographic separation.

Preferably, the reaction products are subjected to a distillative separation. Suitable apparatuses for distillative separation include distillation columns such as tray columns which may be equipped with bubble-cap trays, sieve plates, sieve trays, structure packings or random packings, spinning band columns or evaporators such as thin-film evaporators, falling film evaporators, forced circulation evaporators. Sambay evaporators etc., and combinations thereof. Particular preference is given to using for distillative separation of the reaction products distillation columns, especially spinning band columns.

The 1,1-diarylpropanes of the general formula II that are required as starting material in the process of the invention for preparation of compounds of the general formula I can be purchased commercially or prepared by synthesis routes known from the literature, as known, for example, from DE19742418974.

The invention is elucidated in detail by the examples described hereinafter. These examples are not to be interpreted in such a way as to restrict the invention.

The examples which follow use the following abbreviations:

Dimer 1: 1,1-bis(4-methoxyphenyl)propane

EXAMPLES

I) Preparation Examples

Preparation of 1-methoxy-4-(1-propenyl)benzene (anethole) from 1,1-bis(4-methoxy-phenyl)propane (examples 1-6)

Several cleavage experiments to cleave 1,1-bis(4-methoxyphenyl)propane (Dimer1) to anisole and anethole were conducted. The reactor used was a gas phase oven with an internal diameter of 4 cm and electric heating. The latter was filled first with quartz rings for a distance of 15 cm and then with catalyst strands having a strand diameter of 3 mm for a distance of 20 cm. The part of the gas phase oven filled with quartz rings serves as evaporator zone for the 1,1-bis(4-methoxyphenyl)propane supplied in trickle mode and any solvent added. The carrier gas used was nitrogen. The reaction product was condensed at a temperature of 5° C. in the bottom and in a downstream cooler. When a solvent was used, water in this case, it was run into the evaporator zone together with 1,1-bis(4-methoxyphenyl)propane in two separate feeds. The analysis of the organic products was effected in the experiments after removal and discarding of the aqueous phase.

TABLE 1

Catalyst and reaction conditions of examples 1-12

| Example | Catalyst | T [° C.] | $H_2O$ [ml/h] | Dimer1 [ml/h] | Space velocity [g Dimer1/ g cat./h] | $N_2$ [l/h] |
|---|---|---|---|---|---|---|
| 1 | $SiO_2 \times H_3PO_4$ | 400 | — | 33.0 | 0.500 | 9 |
| 2 | $SiO_2 \times H_3PO_4$ | 450 | — | 32.5 | 0.490 | 10 |
| 3 | $SiO_2 \times H_3PO_4$ | 500 | — | 23.0 | 0.350 | 20 |
| 4 | $SiO_2$ | 450 | — | 16.0 | 0.240 | 20 |
| 5 | $SiO_2$ | 400 | 48.0 | 15.5 | 0.235 | 9 |
| 6 | $SiO_2$ | 400 | 23.2 | 6.4 | 0.097 | 9 |
| 7 | $SiO_2 \times H_3PO_4$ | 350 | 34.2 | 9.9 | 0.26 | 20 |
| 8 | $SiO_2 \times H_3PO_4$ | 400 | 33.2 | 10.6 | 0.28 | 20 |

TABLE 2

Reactant conversion and yields and selectivities of the cleavage products formed

| Example | Conversion of Dimer1 [%] | Anisole Yield [%] | Anisole Selectivity [%] | Anethole isomers Yield [%] | Anethole isomers Selectivity [%] | p-trans-Anethole Yield [%] | p-trans-Anethole Selectivity [%] |
|---|---|---|---|---|---|---|---|
| 1 | 46.3 | 26.7 | 57.6 | 29.8 | 64.4 | 20.3 | 43.9 |
| 2 | 61.0 | 30.6 | 50.2 | 28.7 | 47.0 | 18.6 | 30.5 |
| 3 | 46.1 | 2.9 | 6.3 | 0.9 | 1.8 | 0.5 | 1.2 |
| 4 | 77.1 | 41.0 | 53.2 | 17.3 | 22.4 | 8.9 | 11.5 |
| 5 | 84.9 | 77.3 | 91.0 | 73.6 | 86.7 | 45.1 | 53.1 |
| 6 | 84.5 | 68.3 | 80.8 | 69.1 | 81.8 | 42.8 | 50.6 |
| 7 | 90.5 | — | — | 42.7 | 47.2 | 27.2 | 30.6 |
| 8 | 40.8 | — | — | 31.6 | 77.5 | 22.2 | 54.4 |

Comparative Example C9

As a comparison, the thermal cleavage of 1,1-bis(4-methoxyphenyl)propane to anethole and anisole was reworked by the method described in DE19742418974. For this purpose, 100 g of 1,1-bis(4-methoxyphenyl)propane were initially charged in a glass flask with a connected distillation apparatus and heated to 200° C., and 0.5 g of concentrated phosphoric acid was added. Over the course of the reaction (at least 15 min.), the products formed were distilled off under reduced pressure. At a conversion of 67.3%, a total yield of anetholes (all isomers) of 57.3% was obtained, with the yield of p-trans-anethole of 41.6%.

II) Distillation

A representative reaction output with a p-trans-anethole content of 16.2% by weight (determined by means of GC) was subjected to purifying distillation with the aid of a batch distillation in a 100 cm-long spinning column (about 20 theoretical plates) with safeguard heating, at a pressure at the top of the column of 20 mbar and at the bottom of 2 mbar. The reflux ratio until the removal of anisole was 10:1, and it was increased to 15:1 in order to achieve a higher purity of the product fraction. The maximum bottom temperature was 165° C. The main fraction obtained was two fractions having a p-trans-anethole content of 97.6% by weight (GC content) and 96.5% by weight (GC content). Both corresponded to the characteristic odor profile.

The invention claimed is:

1. A process for preparing arylpropenes of the formula (I)

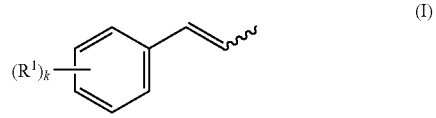

in which k has the values of 0, 1, 2 or 3 and $R^1$ is independently selected from the group consisting of $C_1$-$C_6$-alkoxy, di($C_1$-$C_6$-alkyl)amines and hydroxyl, comprising thermolyzing at least one 1,1-diarylpropane compound of the formula (II)

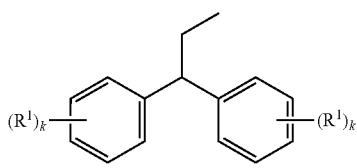

in which k and $R^1$ have the definitions given above, wherein the compound of the formula II in the gas phase is contacted with at least one solid acidic oxidic catalyst in a reaction zone.

2. The process according to claim 1, wherein, in the formulae I and II, k=1 and $R^1$ is hydroxyl or $C_1$-$C_6$-alkoxy.

3. The process according to claim 1, wherein the 1,1-diarylpropane compounds (II) comprise, to an extent of at least 50 mol %, based on the total amount of the compounds of the formula II, compounds of the formula (II.a)

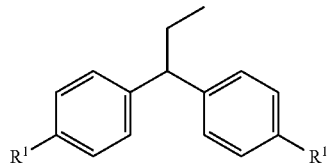

in which both $R^1$ are the same.

4. The process according to claim 1, wherein the reaction zone is supplied, together with the compound of the formula II, additionally with at least one solvent S.

5. The process according to claim 4, wherein the solvent S is water.

6. The process according to claim 4, wherein the mass ratio of solvent S to the compound of the formula II is in the range from 20:1 to 1:100.

7. The process according to claim 1, wherein the catalyst comprises silicon dioxide.

8. The process according to claim 7, wherein the catalyst is a silica which has optionally been impregnated with one or more inorganic acids.

9. The process according to claim 1, wherein the compound of the formula II is contacted with the catalyst at a temperature in the range from 250 to 650° C.

10. The process according to claim 1, wherein the compound of the formula II is conducted continuously through the reaction zone comprising the solid oxidic catalyst.

11. The process according to claim 10, wherein the compound of the formula II is supplied continuously to the reaction zone and the reaction product is quenched immediately after leaving the reaction zone.

12. The process according to claim 10, wherein the compound of the formula II is supplied to the reaction zone with the aid of a carrier gas.

13. The process according to claim 10, wherein the compound of the formula II is conducted through the reaction zone with a catalyst load of 0.01 to 5 kg of compound II per kg of catalyst and hour.

14. The process according to claim 1, wherein, in the formulae I and II, k=1 and $R^1$ is hydroxyl or methoxy.

* * * * *